United States Patent
Mørk et al.

(10) Patent No.: US 6,844,352 B2
(45) Date of Patent: Jan. 18, 2005

(54) 1'-[4-[1-(4-FLUOROPHENYL)-1H-INDOLE-3-YL]-1-BUTYL]-SPIRO[ISOBENZOFURAN-1(3H),4'-PIPERIDINE] HYDROHALOGENIDES

(75) Inventors: Niels Mørk, Virum (DK); Heidi Lopez de Diego, Kokkedal (DK); Ole Nielsen, Valby (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

(21) Appl. No.: 10/272,403

(22) Filed: Oct. 15, 2002

(65) Prior Publication Data

US 2003/0055074 A1 Mar. 20, 2003

Related U.S. Application Data

(63) Continuation of application No. 09/564,364, filed on Apr. 28, 2000, now abandoned, which is a continuation of application No. PCT/DK98/00480, filed on Nov. 6, 1998.

(30) Foreign Application Priority Data

Nov. 7, 1997 (DK) .............................................. 1267/97

(51) Int. Cl.⁷ ..................... A61K 31/454; C07D 401/06
(52) U.S. Cl. ......................................... 514/278; 546/18
(58) Field of Search .............................. 546/18; 514/278

(56) References Cited

U.S. PATENT DOCUMENTS 5,665,725 A    9/1997  Moltzen et al. .............. 514/278

FOREIGN PATENT DOCUMENTS

WO          92/22554        12/1992

OTHER PUBLICATIONS

Ejner K. Moltzen, et al., *J. Med. Chem.* 28: 2009–2017 (1995).

Jens Perregaard et al., "σ Ligands with Subnanomolar Affinity and Preference for the σ₂ Binding Site 1.3–ω Aminoalkyl)–1H–indoles," *J. Med. Chem.* 38: 1998–2008 (1995).

*Primary Examiner*—Patricia L. Morris
(74) *Attorney, Agent, or Firm*—Darby & Darby

(57) ABSTRACT

The present invention relates to a hydrohalogenide of 1'-[4-[1-(4-fluorophenyl)-1H-indole-3-yl]-1-butyl]-spiro[isobenzofuran-1(3H),4'-piperidine], pharmaceutical compositions containing the acid addition salts and the use thereof for the treatment of psychic and neurological disorders.

4 Claims, No Drawings

1'-[4-[1-(4-FLUOROPHENYL)-1H-INDOLE-3-YL]-1-BUTYL]-SPIRO[ISOBENZOFURAN-1(3H),4'-PIPERIDINE] HYDROHALOGENIDES

This is a continuation of application Ser. No. 09/564,364, filed Apr. 28, 2000, now abandoned, which is a continuation of international application no. PCT/DK98/00480, filed Nov. 6, 1998. These prior applications are hereby incorporated herein by reference, in their entirety.

The present invention relates to hydrohalogenides of 1'-[4-[1-(4-fluorophenyl)-1H-indole-3-yl]-1-butyl]-spiro[isobenzofuran-1(3H),4'-piperidine] with hydrochloric, hydrobromic, or hydroiodic acid, pharmaceutical compositions containing the acid addition salts and the use thereof for the treatment of psychic and neurological disorders.

BACKGROUND OF THE INVENTION

International Patent Publication No. WO 92/22554 discloses a series of sigma receptor ligands which are considered useful for the treatment of a range of psychic and neurological disorders. The structure activity relationship of these compounds has been further investigated by Perregaard, J. et al., *J. Med. Chem.* 1995, 38, 11, p. 1998–2008.

One of the compounds herein, which is the subject of the present invention, has the general formula

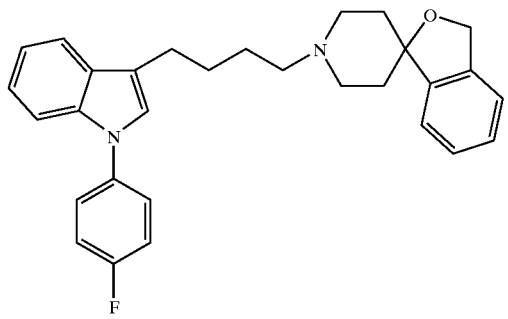

This compound was shown in Perregaard, J. et al., *J. Med. Chem.* 1995, 38, 11, p. 1998–2008 to be a potent and selective sigma ligand. Furthermore, the anxiolytic potential of the compound was tested in the black/white exploration test in rats, which is an animal model predictive for anxiolytic activity, and was found to be active over a large dose range.

Evidence has been presented from studies of the biology and function of sigma receptors that sigma receptor ligands may be useful in the treatment of a range of psychic and neurological disorders, including psychosis and movement disorders, such as dystonia and tardive dyskinesia, and motor disturbances associated with Huntington's chorea or Tourette's syndrome and in Parkinson's disease (Walker, J. M. et al, *Pharmacological Reviews,* 1990, 42, 355). The known sigma receptor ligand rimcazole clinically shows effect in the treatment of psychoses (Snyder, S. H., Largent, B. L. *J. Neuropsychiatry* 1989, 1, 7) and a group of sigma receptor ligands have been described to show antihallucinogenic activity in animal models (International Patent Publication No. WO 9103243).

Sigma receptor ligands have also been reported to be involved in modulation of NMDA receptor mediated events in the brain and to act as anti-ischemic agents in in vivo tests (Rao, T. S. et al, *Molecular Pharmacology,* 1990, 37, 978). In addition to ischemia they may also be useful in the treatment of other such NMDA receptor mediated events, e.g. epilepsy and convulsion.

Also, some sigma receptor ligands have been found to show anti-amnesic effects in an animal model (Early et al., *Brain Research* 1991, 546, 281–286).

Sigma ligands have been shown to influence central acetylcholine levels in animal models (Matsuno et al, *Brain Research* 1992, 575, 315–319; Junien et al, *Eur. J. Pharm.* 1991, 200, 343–345) and may therefore have potential in the treatment of senile dementia of the Alzheimer type.

Finally, some guanidine derivatives having sigma receptor activity have been disclosed to be useful as anxiolytics (International Patent Publication No. WO 9014067).

Accordingly, a compound which acts potently on the sigma receptors in the central nervous system is believed to be of potential use in the treatment of anxiety, psychosis, epilepsy, convulsion, movement disorders, motor disturbances, amnesia, cerebrovascular diseases, senile dementia of Alzheimer type and Parkinson's disease.

The free base of 1'-[4-[1-(4-fluorophenyl)-1H-indole-3-yl]-1-butyl]-spiro[isobenzofuran-1(3H),4'-piperidine] is an oil and as such not useful for the production of solid pharmaceutical preparations, such as tablets or capsules. As oral administration of a solid entity is the preferred and most convenient method for the administration of a pharmaceutical, a solid form of the compound, suitably a pharmaceutically acceptable salt thereof, which can be mixed with various adjuvants or diluents and formed into tablets or filled in capsules, is highly desirable.

The compound, 1'-[4-[1-(4-fluorophenyl)-1H-indole-3-yl]-1-butyl]-spiro[isobenzofuran-1(3H),4'-piperidine] was disclosed for the first time in International Patent Publication No. WO 92/22544 (compound No. 5a) in the form of the oxalic acid addition salt.

Another acid addition salt of 1'-[4-[1-(4-fluorophenyl)-1H-indole-3-yl]-1-butyl]-spiro[isobenzofuran-1(3H),4'-piperidine], namely the fumarate has been disclosed in Perregaard, J. et al., *J. Med. Chem.* 1995, 38, 11, p. 1998–2008.

The aqueous solubility of both the free base and the fumarate is very low, a property which is known to possibly compromise the bioavailability of the drug. Furthermore, experiments in rats and dogs have indicated a limited bioavailablity of the fumarate of 1'-[4-[1-(4-fluorophenyl)-1H-indole-3-yl]-1-butyl]-spiro[isobenzofuran-1(3H),4'-piperidine].

It has now, surprisingly, been found that the relative bioavailability of the hydrochloride of 1'-[4-[1-(4-fluorophenyl)-1H-indole-3-yl]-1-butyl]-spiro[isobenzofuran-1(3H),4'-piperidine] is three times larger than that of the fumarate salt.

The hydrochloride of the invention also have improved water solubility compared to the fumarate of 1'-[4-[1-(4-fluorophenyl)-1H-indole-3-yl]-1-butyl]-spiro[isobenzofuran-1(3H),4'-piperidine].

THE INVENTION

According to the present invention new hydrohalogenides of 1'-[4-[1-(4-fluorophenyl)-1H-indole-3-yl]-1-butyl]-spiro[isobenzofuran-1(3H),4'-piperidine] with improved bioavailability has been provided.

In a particularly preferred embodiment of the invention the acid addition salt according to the invention is the hydrochloride of 1'-[4-[1-(4-fluorophenyl)-1H-indole-3-yl]-1-butyl]-spiro[isobenzofuran-1(3H),4'-piperidine].

In another embodiment of the invention relates to the hydrobromide of 1'-[4-[1-(4-fluorophenyl)-1H-indole-3-yl]-1-butyl]-spiro[isobenzofuran-1(3H),4'-piperidine].

The invention also relates to pharmaceutical compositions containing the hydrohalogenide salts of the invention and the use of the salts for the preparation of pharmaceutical compositions and the use thereof for the treatment of anxiety, psychoses, epilepsy, convulsion, movement disorders, motor disturbances, amnesia, cerebrovascular diseases, senile dementia of Alzheimer type and Parkinson's disease.

As used herein, a hydrohalogenide of 1'-[4-[1-(4-fluorophenyl)-1H-indole-3-yl]-1-butyl]-spiro[isobenzofuran-1(3H),4'-piperidine] means the hydrochloride, the hydrobromide or the hydroiodide of 1'-[4-[1-(4-fluorophenyl)-1H-indole-3-yl]-1-butyl]-spiro[isobenzofuran-1(3H),4'-piperidine] and includes the anhydrate, the hemi-, mono- and dihydrate thereof as well as solvents thereof.

The hydrohalogenides according to the invention may be obtained by treatment of 1'-[4-[1-(4-fluorophenyl)-1H-indole-3-yl]-1-butyl]-spiro[isobenzofuran-1(3H),4'-piperidine] with hydrochloric, hydrobromic or hydroiodic acid in an inert solvent followed by precipitation, isolation and optionally recrystallization by known methods and if desired micronisation of the crystalline product by wet or dry milling or another convenient process, or preparation of particles from a solvent-emulsification process.

Precipitation of the hydrohalogenide addition salt is preferably carried out in an inert solvent, e.g. an inert polar solvent such as an alcohol (e.g. ethanol, 2-propanol and n-propanol).

According to the invention, hydrohalogenides of 1'-[4-[1-(4-fluorophenyl)-1H-indole-3-yl]-1-butyl]-spiro[isobenzofuran-1(3H),4'-piperidine] may be administered in any suitable way e.g. orally or parenterally, and the salt may be presented in any suitable form for such administration, e.g. in the form of tablets, capsules, powders, syrups or solutions or dispersions for injection. Preferably, and in accordance with the purpose of the present invention, the salt of the invention is administered in the form of a solid pharmaceutical entity, suitably as a tablet or a capsule.

Methods for the preparation of solid pharmaceutical preparations are well known in the art. Tablets may thus be prepared by mixing the active ingredients with ordinary adjuvants and/or diluents and subsequently compressing the mixture in a convenient tabletting machine. Examples of adjuvants or diluents comprise: corn starch, lactose, talcum, magnesium stearate, gelatine, lactose, gums, and the like. Any other adjuvant or additive such as colourings, aroma, preservatives, etc. may also be used provided that they are compatible with the active ingredients.

The salts of the invention are most conveniently administered orally in unit dosage forms such as tablets or capsules, containing the active ingredient in an amount from about 10 μg/day/kg to 25 mg/day/kg body weight, or between 25 μg/day/kg to 10 mg/day/kg body weight. A suitable daily dose is between 1.0 and 160 mg/day.

The invention will be illustrated in the following examples. The examples may not be construed as limiting.

The fumarate of 1'-[4-[1-(4-fluorophenyl)-1H-indole-3-yl]-1-butyl]-spiro[isobenzofuran-1(3H),4'-piperidine] can be prepared as described in Perregaard, J. et al., *J. Med. Chem.* 1995, 38, 11, p. 1998–2008 (compound 14f).

EXAMPLE 1

1'-[4-[1-(4-fluorophenyl)-1H-indole-3-yl]-1-butyl]-spiro[isobenzofuran-1(3H),4'-piperidine]

1'-[4-[1-(4-fluorophenyl)-1H-indole-3-yl]-1-butyl]-spiro[isobenzofuran-1(3H),4'-piperidine], fumarate (69 g) was suspended in water (350 ml) and ethylacetate (350 ml). The mixture was made alkaline (pH 10–12) by the addition of concentrated aqueous sodium hydroxide and stirred until all solids were dissolved. The aqueous layer was extracted with ethylacetate (2×100 ml) and the combined organic extracts were dried over sodium sulphate and evaporated in vacuo.

EXAMPLE 2

1'-[4-[1-(4-fluorophenyl)-1H-indole-3-yl]-1-butyl]-spiro[isobenzofuran-1(3H),4'-piperidine], hydrochloride 1'-[4-[1-(4-fluorophenyl)-1H-indole-3-yl]-1-butyl]-spiro[isobenzofuran-1(3H),4'-piperidine] (10.3 g) and 2-propanole (100 ml) were heated to reflux. The solution was allowed to cool to 45° C. Aqueous hydrochloric acid (2.2 ml, 36%) was added dropwise and a precipitate of the title compound was formed. The suspension was heated to reflux and allowed to cool to ambient temperature. The suspension was cooled in ice, filtered off and dried. Yield: 10.1 g (90%). The salt is a mono salt and according to our investigations an anhydrate. KF: 0.51%; HPLC 100.8%; DSC (onset/peak$_{max}$) 222.5° C./223.8° C. CHN (calculated/measured): C: 73.38/73.13; H: 6.57/6.56; N: 5.70/5.80.

EXAMPLE 3

1'-[4-[1-(4-fluorophenyl)-1H-indole-3-yl]-1-butyl]-spiro[isobenzofuran-1(3H),4'-piperidine] hydrobromide 1'-[4-[1-(4-fluorophenyl)-1H-indole-3-yl]-1-butyl]-spiro[isobenzofuran-1(3H),4'-piperidine](1.05 g, oil) and 2-propanole (10 ml) was stirred and heated until the oil was dissolved. Aqueous hydrobromic acid (2.5 ml, 47% HBr) was added dropwise and a precipitate of the title compound was formed. More 2-propanole (5 ml) and hydrobromic acid (2.5 ml, 47% HBr) was added to the suspension. The suspension was cooled on ice and the precipitate was filtered off and dried.

EXAMPLE 4

1'-[4-[1-(4-fluorophenyl)-1H-indole-3-yl]-1-butyl]-spiro[isobenzofuran-1(3H),4'-piperidine] hydroiodide 1'-[4-[1-(4-fluorophenyl)-1H-indole-3-yl]-1-butyl]-spiro[isobenzofuran-1(3H),4'-piperidine] (1.0 g, oil) and 2-propanole (15 ml) was stirred and heated until the oil was dissolved. Aqueous hydroiodic acid (1 ml, 57% HI) was added dropwise and crystals of the title compound was formed. More 2-propanole (10 ml) and hydrobromic acid (4 ml, 57% HI) was added to the suspension. The suspension was cooled on ice and the precipitate was filtered off and dried.

Bioavailability Study

After multiple administration in Beagle dogs, the bioavailability of the salts of 1'-[4-[1-(4-fluorophenyl)-1H-indole-3-yl]-1-butyl]-spiro[isobenzofuran-1(3H),4'-piperidine] was investigated as described in the following study:

Two groups, each consisting of four Beagle dogs (2 males and 2 females) were used in the study.

The dogs in the individual groups were given single daily doses of 10 mg/kg/day (calculated as free base) of the fumarate and the hydrochloride of 1'-[4-[1-(4-fluorophenyl)-1H-indole-3-yl]-1-butyl]-spiro[isobenzofuran-1(3H),4'-piperidine] for seven days.

Blood samples for serum preparation were drawn from the test animals at specific nominal time points before and after dosing on each day and analyzed using HPLC.

Test Animals

Four male and four female purpose-bred Beagle dogs all from Interfauna, Ltd., Huntingdon, UK were allocated at random in pairs to one of the two study groups.

At the start of the treatment, the dogs were approximately 12–38 months old and weighed 9.8-13.0 kg.

Dose and Formulation

Single doses of the different salts corresponding to 10.0 mg (~21997 nmol) of 1'-[4-[1-(4-fluorophenyl)-1H-indole-3-yl]-1-butyl]-spiro[isobenzofuran-1(3H),4'-piperidine] per kg body weight were accurately weighed into gelatine capsules. The calculated amounts of test compound for each dog were based on body weights measured at study start.

Dosing

The test animals were dosed once daily between 08:00 and 09:00 (24-hour clock) for 7 days.

Blood Sampling and Serum Preparation

Blood samples (approx. 3 ml) for serum preparation were drawn from the jugular vein of the test animals at the following nominal time points before and after dosing on each day:

| Day 1:   | Before, 1, 2, 3, 4, 6, 8 and 12 hours after dosing. |
|----------|------------------------------------------------------|
| Day 2–6: | Before and 3 hours after dosing.                     |
| Day 7:   | Before, 1, 2, 3, 4, 6, 8, 12, 24, 48, 72 and 96 hours after dosing. |

The time points above corresponds to: before, 1, 2, 3, 4, 6, 8, 12, 24, 27, 48, 51, 72, 75, 96, 99, 120, 123, 144, 145, 146, 147, 148, 150, 152, 156, 168, 192, 216 and 240 hours after the first dosing on day 1.

The exact blood sampling times for each dog relative to the first dose were recorded.

Blood samples were allowed to clot at room temperature for 30–90 minutes after sampling. The clotted samples were centrifuged at 1000 g for 15 minutes and separated serum transferred to clean test tubes. Serum samples were stored at approx. −20° C. until analysis.

Drug Assay

The serum samples obtained were analysed for content of 1'-[4-[1-(4-fluorophenyl)-1H-indole-3-yl]-1-butyl]-spiro[isobenzofuran-1(3H),4'-piperidine] by a pseudo-normal phase HPLC-method after liquid-liquid extraction. 1'-[4-[1-(4-fluorophenyl)-1H-indole-3-yl]-1-buty]-spiro[5-fluoro-isobenzofuran-1(3H),4'-piperidine] was used as internal standard. Serum samples were analysed for content of 1'-[4-[1-(4-fluorophenyl)-1H-indole-3-yl]-1-butyl]-spiro[isobenzofuran-1(3H),4'-piperidine] using the following reference substances, extraction procedure and high performance liquid chromatographic (HPLC) method.

Reference Substances

1'-[4-[1-(4-fluorophenyl)-1H-indole-3-yl]-1-butyl]-spiro[isobenzofuran-1(3H),4'-piperidine], fumarate, 1'-[4-[1-(4-fluorophenyl)-1H-indole-3-yl]-1-butyl]-spiro[5-fluoro-isobenzo-furan-1(3H),4'-piperidine] (ISTD), 1'-[5-phenyl-1-pentyl]-spiro[isobenzo-furan-1(3H),4'-piperidine] (stabilising agent).

Extraction Procedure

Ethanol (50 μl), 100 μl 2 N NaOH and 4.0 ml n-heptane containing 1% isobutanol was added to serum samples of 500 μl. The samples were shaken for 15 minutes, centrifuged for 5 minutes at approximately 2000 g and then frozen in an ethanol/dry ice bath. The organic phase was transferred to a clean test tube and evaporated under nitrogen ($N_2$) at 40° C. The residue was dissolved in 150 μl mobile phase for HPLC (se below) and 75 μl analysed by HPLC.

| HPLC method | |
|---|---|
| Column: | HP Hypersil (100 × 4.6 mm I.D., 5 μm particles) |
| Column temperature: | 35° C. |
| Mobile phase composition: | Acetonitrile: 0.25 M Ammonium acetate (98:2 v/v) |
| Mobile phase flow: | 1.0 ml/min |
| Detection: | Fluorescence (Excitation: 257 nm, Emission: 380 nm) |
| Injection volume: | 75 μl |
| Runtime: | 14 min |
| Retention time: | 1'-[4-[1-(4-fluorophenyl)-1H-indol-3-yl]-1-butyl]-spiro[isobenzofuran-1(3H),4'-piperidine]: ~9.7 min, 1'-[4-[1-(4-fluorophenyl)-1H-indol-3-yl]-1-butyl]-spiro[5-fluoroisobenzofuran-1(3H),4'-piperidine] (ISTD): ~6.5 min. |

All serum samples were analysed as single determinations.

The limit of quantification was 2 ng per sample for 1'-[4-[1-(4-fluorophenyl)-1H-indole-3-yl]-1-butyl]-spiro[isobenzofuran-1(3H),4'-piperidine] corresponding to 8.80 nmol/l serum using 500 μl serum for analysis.

Calibration samples for calculation of serum concentrations of 1'-[4-[1-(4-fluorophenyl)-1H-indole-3-ly]-1-butyl]-spiro[isobenzofuran-1(3H),4'-piperidine] were prepared and analysed on each day of analysis from control dog serum spiked with known amounts of 1'-[4-[1-(4-fluorophenyl)-1H-indole-3-yl]-1-butyl]-spiro[isobenzofuran-1(3H),4'-piperidine] in the range 0–500 ng of each compound per sample.

Quality control (QC) samples were prepared and analysed on each day of analysis from control dog serum spiked with known amounts (1, 50 or 400 ng per sample) of 1'-[4-[1-(4-fluorophenyl)-1H-indole-3-yl]-1-butyl]-spiro[isobenzofuran-1(3H),4'-piperidine.

Calculation

Serum concentrations of 1'-[4-[1-(4-fluorophenyl)-1H-indole-3-yl]-1-butyl]-spiro[isobenzofuran-1(3H),4'-piperidine] (ng/ml and nmol/l) were calculated from the actual amounts (ng) found by analysis and the serum volume used for analysis.

The area under the serum concentration versus time curve from time zero to 24 hours after dosing on day 7 ($AUC_{0-24,7}$) was calculated by the linear trapezoidal rule.

The relative oral bioavailability of 1'-[4-[1-(4-fluorophenyl)-1H-indole-3-yl]-1-butyl]-spiro[isobenzofuran-1(3H),4'-piperidine] ($F_{rel}$) of the hydrochloride compared to the bioavailability of the fumarate salt was estimated as the ratio between the mean $AUC_{0-24,7}$ values found for the group of dogs which had received the hydro chloride and the mean $AUC_{0-24.7}$ value found for group of dogs which had received the fumarate.

Results are presented in table 1:

TABLE 1

Relative bioavailability ($F_{rel}$) of a hydrochloride of 1'-[4-[1-(4-fluorophenyl)-1H-indole-3-yl]-1-butyl]-spiro[isobenzofuran-1(3H),4'-piperidine] after oral administration.

| Acid addition salt | $AUC_{0-24.7}$ | | $F_{rel}$ |
|---|---|---|---|
| | Mean | SD | (compared to fumarate) |
| Fumarate | 4017 | 2403 | — |
| Hydrochloride | 12023 | 3699 | 2.99 |

What is claimed is:

1. A hydrohalogenide of 1'-[4-[1-(4-fluorophenyl)-1H-indole-3-yl]-1-butyl]-spiro[isobenzofuran-1(3H),4'-piperidine], or hydrate thereof.

2. The hydrohalogenide of claim 1 which is the hydrochloride of 1'-[4-[1-(4-fluorophenyl)-1H-indole-3-yl]-1-butyl]-spiro[isobenzofuran-1(3H),4'-piperidine], or hydrate thereof.

3. A pharmaceutical composition comprising a hydrohalogenide of claim 1 and a pharmaceutically acceptable carrier or diluent.

4. The pharmaceutical composition of claim 3 wherein the hydrohalogenide is the hydrochloride.

* * * * *